United States Patent [19]
Dorin et al.

[11] Patent Number: 4,894,439
[45] Date of Patent: * Jan. 16, 1990

[54] N-TERMINAL DERIVATIVES OF TUMOR NECROSIS FACTOR PURIFIED BY MICROPOROUS PTFE MEMBRANES

[75] Inventors: Glenn Dorin, San Rafael, Calif.; Wolfgang H. Hanisch, Brisbane, Australia; James W. Thomson, Albany, Calif.; Sidney N. Wolfe, El Cerrito, Calif.; Leo S. Lin, Walnut Creek, Calif.

[73] Assignee: Cetus Corporation, Emeryville, Calif.

[ * ] Notice: The portion of the term of this patent subsequent to Jun. 30, 2004 has been disclaimed.

[21] Appl. No.: 866,213

[22] Filed: May 22, 1986

[51] Int. Cl.⁴ .............................................. C07K 13/00
[52] U.S. Cl. ................................... 530/351; 530/412; 530/416; 530/417; 530/820; 530/825; 435/68; 435/70
[58] Field of Search ....................... 530/351, 820, 825; 435/68, 70

[56] References Cited

U.S. PATENT DOCUMENTS

| | | |
|---|---|---|
| 4,289,690 | 9/1981 | Pestka et al. ........................ 424/85 |
| 4,309,418 | 1/1982 | Green ................................. 424/101 |
| 4,495,282 | 1/1985 | Ohnishi et al. ...................... 435/68 |
| 4,677,063 | 6/1987 | Mark et al. .......................... 530/351 |
| 4,677,064 | 6/1987 | Mark et al. .......................... 530/351 |
| 4,677,197 | 6/1987 | Lin et al. ............................. 530/417 |

FOREIGN PATENT DOCUMENTS

| | | |
|---|---|---|
| 131789 | 1/1985 | European Pat. Off. |
| 148311 | 7/1985 | European Pat. Off. |
| 155549 | 9/1985 | European Pat. Off. |
| 158286 | 10/1985 | European Pat. Off. |
| 168214 | 1/1986 | European Pat. Off. |
| 0168214 | 1/1986 | European Pat. Off. |
| WO85/05631 | 12/1985 | PCT Int'l Appl. |
| WO86/03751 | 7/1986 | PCT Int'l Appl. |
| 2106117 | 4/1983 | United Kingdom |

OTHER PUBLICATIONS

Sofer et al, pi Bio/Techniques, 1983, pp. 198–201.
Bunneyear et al., Bio/Technology, 4, 1986, pp. 954–958.
Ruben et al., PNAS, 82, 1985, pp. 6637–6641.
Eur. J. Biochem 152, 1985, pp. 515–522, Marmenout et al.
Aggawal et al., JBC 260, 1985, pp. 2345–2354.
Minobe et al, J. Chromato. 248, 1982, pp. 401–408.
Bio Rad Bulletin, #1153.
Borg et al, Can. J. Physiol Pharmacol 59, 1981, pp. 890–892.
Issekutz, J. Immunol Methods 61(1983), pp. 275–281.
Pharmacia Bio Technology Products Catalog 86.
Pennica, D. et al., Nature, 312, 20/27 Dec. 1984, pp. 724–729.
Wang et al., Science (1985), 228:149–154.
Matthews, N., Br. J. Cancer (1981) 44:418.
Williamson et al., PNAS, 80, 5397–5401 (1983).
Shirai et al., Nature, 313, 803 (1985).
Abe et al., FEBS Letters 180, 203–206 (1985).

Primary Examiner—Garnette D. Draper
Attorney, Agent, or Firm—Gregory J. Giotta; Elliott L. Fineman; Albert P. Halluin

[57] ABSTRACT

A process is disclosed for the purification of recombinantly produced biologically active proteins in which a solution containing a mixture of materials, including the biologically active protein, is passed through a continuous porous hydrophobic membrane, and the fraction enriched in the biologically active protein is recovered. Hydrophobic proteins such as TNF and recombinant ricin toxin A chain may be purified according to the process. Conditions for enhanced recovery of purified TNF using the process are disclosed. A highly purified TNF comprising 95% or greater TNF as determined by SDS-PAGE analysis, with an endotoxin content of less than 0.1 ng/mg TNF which is substantially free of pyrogens by the USP rabbit pyrogen test at a dosage range of 1.0 to $2.4 \times 10^5$ U/kg, is obtained.

9 Claims, 5 Drawing Sheets

Figure 1

```
      ▽1 ▽2 ▽3 ▽4  ▽5 ▽6▽7  ▽8  ▽9▽10
       ↓  ↓  ↓  ↓   ↓  ↓ ↓   ↓   ↓  ↓
  1  VALARGSERSER SERARGTHRPRO SERASPLYSPRO VALALAHISVAL VALALAASNPRO
                                  ▽ 31
                                  ↓
 21  GLNALAGLUGLY GLNLEUGLNTRP LEUASNARGARG ALAASNALALEU LEUALAASNGLY

41  VALGLULEUARG ASPASNGLNLEU VALVALPROSER GLUGLYLEUTYR LEUILETYRSER
                                 ALA 69
                                 SER 69
 61  GLNVALLEUPHE LYSGLYGLNGLY CYSPROSERTHR HISVALLEULEU THRHISTHRILE

81  SERARGILEALA VALSERTYRGLN THRLYSVALASN LEULEUSERALA ILELYSSERPRO
       ALA101
       SER101
101  CYSGLNARGGLU THRPROGLUGLY ALAGLUALALYS PROTRPTYRGLU PROILETYRLEU

121  GLYGLYVALPHE GLNLEUGLULYS GLYASPARGLEU SERALAGLUILE ASNARGPROASP
      ▽ 140                     ▽ 150                    ▽ 156
      ↓                         ↓                        ↓
141  TYRLEUASPPHE ALAGLUSERGLY GLNVALTYRPHE GLYILEILEALA LEU
```

| LANE NO. | SAMPLE |
|---|---|
| 1 | MW Standard |
| 2 | TNF Control |
| 3 | Blank |
| 4 | Purified Product (reducing gel) |
| 5 | Purified Product (reducing gel) |
| 6 | Purified Product (reducing gel) |
| 7 | Blank |
| 8 | Purified Product (nonreducing gel) |
| 9 | Purified Product (nonreducing gel) |
| 10 | Purified Product (nonreducing gel) |
| 11 | Blank |
| 12 | TNF Control |
| 13 | MW Standard |
| 14 | Blank |

N-TERMINAL DERIVATIVES OF TUMOR NECROSIS FACTOR PURIFIED BY MICROPOROUS PTFE MEMBRANES

FIELD OF THE INVENTION

This invention relates to a process for the purification of biologically active proteins. In particular, it relates to a process for the purification and recovery of polypeptides having the biological activity of tumor necrosis factor (TNF). The process disclosed herein is especially useful in the recovery of substantially pure homogeneous biologically active recombinant TNF which is free of pyrogenic activity other than that which may be caused by TNF itself. The invention also relates to the substantially pure homogeneous biologically active TNF which is free of pyrogenic activity other than that which ray be caused by TNF itself. The invention furthermore relates to a process for the purification of biologically active proteins that are hydrophobic at physiological pH, such proteins being in this regard like TNF.

BACKGROUND OF THE INVENTION

Processes for the purification of proteins are generally known and include such techniques as ion exchange chromatography, adsorption chromatography, gel electrophoresis, ammonium sulfate precipitation, and gel filtration.

Although each of these techniques is known, it is impossible to predict the extent to which any of the above-listed techniques is applicable to the purification of a given protein. Various factors including the extent of purification desired, the extent of acceptable loss of biological activity of the protein, and degree of homogeneity of the protein desired, require extensive experimentation to optimize the purification of the products.

Human TNF has been purified as a native protein from culture supernatants of induced HL-60 cells by a combination of anion exchange chromatography and reverse phase high pressure liquid chromatography (HPLC), with elution in a linear gradient of acetonitrile (Wang, A. M., et al., *Science* (1985) 228:149–154). Similar procedures had been previously employed (Matthews, N., *Br. J. Cancer* (1981) 44:418) without resulting in a homogeneous preparation. However, this technique is not optimally efficient even for the native TNF secreted from, for example, HL-60 or other TNF secreting cell lines, and is inappropriate for recombinantly produced TNF, due to substantial inactivation of TNF biological activity at low pH.

Copending U.S. application Ser. No. 792,815 filed Oct. 20, 1985 now U.S. Pat. No. 4,677,197 and assigned to the same assignee of the present application improves upon the process of Wang et al. supra. Whereas Wang et al. obtain a product that is not homogeneous by the steps of anion exchange chromatography, followed by HPLC and elution in a linear acetonitrile gradient, U.S. application Ser. No. 792,815 achieves an active homogeneous recombinantly produced TNF product. In the improved process according to U.S. application Ser. No. 792,815 a hydrophobic support is substituted for the reverse phase HPLC of Wang, M. et al., supra and Matthews, N. et al., supra.

European Patent Publication No. 168,214 published Jan. 15, 1986 discloses a process for purifying TNF by the steps of obtaining a TNF solution from cell culture supernatants or lysates, removing solids, adsorbing TNF from the remaining supernatant onto a silicate support, eluting TNF from the silicate support, chromatographing TNF on a tertiary amino anion exchange resin, and chromatographing TNF on an anion exchange resin containing quaternary ammonium substituents. Optional purification steps including chromatofocusing to concentrate and purify the product or passage through a sieving gel such as Sephadex G-25 are disclosed. As a hydrophobic support, EP Publication 168,214 discloses the use of silicate, polyolefin and alkyl Sepharose. The TNF is eluted from the silicate using a polyol, preferably ethylene glycol in a 10–30% range, with a 20% (v/v) concentration preferred. Further purification, according to the process, requires adsorption onto a tertiary or quaternary amino anion exchange resin such as DEAE cellulose, QAE Sephadex or the product sold under the tradename Mono Q. Purification to homogeneity, according to the process, is accomplished only upon further separation on sodium dodecyl sulfate-polyacrylamide gel electrophoresis (SDS-PAGE) or C4 reverse phase high performance liquid chromatography (HPLC). These latter steps are accompanied, however, by substantial loss of biological activity.

The present invention provides a method for purifying TNF that produces a substantially homogeneous TNF without recourse to reverse phase HPLC or SDS-PAGE electrophoresis. The method disclosed is applicable to large scale purification of TNF. When the host cell is a Gram-negative microorganism such as *E. coli* and the TNF is thus recombinantly produced, a number of host cell proteins and other substances are produced with the TNF. Such co-produced materials include endotoxins and pyrogenic materials that must be selectively removed from the TNF. The use of a filtration step through a hydrophobic porous matrix, offers substantial recovery of active TNF proteins and substantially complete removal of host cell proteins, endotoxins and pyrogens when the host cell is a Gram-negative microorganism, before the use of any chroaatographic techniques in purifying the TNF. As a result, large scale recovery of the material is possible.

BRIEF DESCRIPTION OF THE INVENTION

The process according to the invention is used to obtain a partially purified TNF from a TNF containing fluid obtained from a recombinant host and comprises the step of passing the TNF containing fluid through a continuous hydrophobic porous matrix, and recovering the partially purified TNF therefrom.

In another aspect, the invention includes the partially purified TNF produced by the process. The partially purified TNF comprises a least about 20% of the TNF produced by the recombinant host cells, and about 40 to 50% of the total recovered protein, and has an endotoxin content of 10 ng/ml-10 $\mu$g/ml.

In another aspect, the invention is a process for obtaining a purified TNF from a TNF containing fluid obtained from a recombinant host cell comprising the steps of passing the TNF-containing fluid through a continuous hydrophobic porous matrix to produce a partially purified TNF, further purifying said partially purified TNF by at least one hydrophobic interaction matrix chromatography step and at least one anion exchange matrix chromatography step, and recovering a purified TNF having a TNF content of at least 95% as determined by SDS-PAGE analysis and an endotoxin content of less than 0.1 ng/mg TNF.

In one embodiment of this process, the anion exchange chromatography step preceeds the hydrophobic interaction matrix chromatography step.

In another embodiment of this process, the hydrophobic interaction matrix chromatography step preceeds the anion exchange chromatographic step.

Other optional steps of the process according to the invention include size exclusion chromatography and concentration steps. Additional anion exchange chromatography steps may be used in the further purification as is disclosed in greater detail hereinbelow.

In yet another aspect, the invention is a purified recombinant TNF composition having a TNF content of at least 95% as determined by SDS-PAGE analysis, an endotoxin content of less that about 0.1 nanograms/mg, said TNF being substantially free or pyrogens as determined by the USP rabbit pyrogen test at a dosage range of 1.0 to $2.4 \times 10^5$ U/Kg. The TNF produced is substantially similar to mature TNF or may contain modifications to the molecule, particularly N- terminal sequence deletions and substitution in amino acids.

In another aspect, the invention relates to a process for obtaining a partially purified TNF under pH conditions that reduce hydrolysis of the TNF. The pH is controlled so that it is greater than 5.5 during the first stage of the process in which TNF-producing cells are disrupted, the cell debris is removed therefrom, and the retaining fluid is diafiltered through a hydrophobic porous matrix, preferably a continuous hydrophobic porous matrix, to produce a filtrate.

In still another aspect, the invention relates to a process for obtaining partially purified biologically active proteins wherein such proteins are produced in a recombinant host, comprising the step of passing a fluid containing the biologically active protein through a continuous hydrophobic porous matrix and recovering the partially purified biologically active protein.

In yet still another aspect, the invention relates to a process for obtaining partially purified biologically active proteins that are hydrophobic at physiological pH wherein such proteins are produced in a recombinant host, comprising the step of passing a fluid containing the biologically active protein obtained from a recombinant host through a continuous hydrophobic porous matrix and recovering the partially purified biologically active protein.

BRIEF DESCRIPTION OF THE DRAWINGS

FIG. 1 shows the amino acid sequence of mature TNF and a number of N-terminally deleted muteins.

DETAILED DESCRIPTION OF THE INVENTION

General Terms and Techniques

Figure 2:
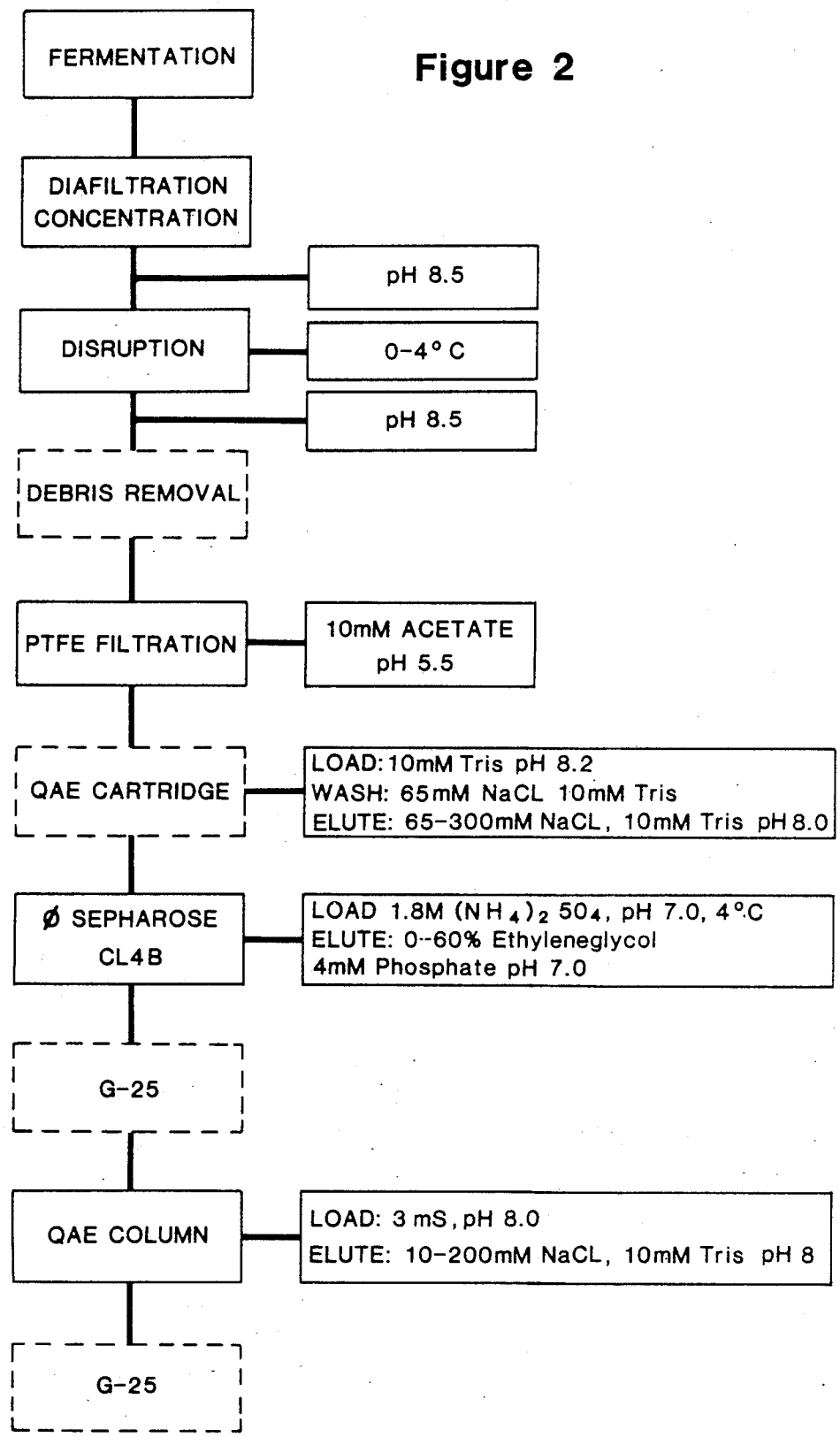
FIG. 2 is a flow diagram of a preferred TNF purification process. Optional steps in the preferred process are denoted by a broken line.

As used herein, the term "tumor necrosis factor" refers to a molecule that is substantially equivalent to the amino acid sequence of FIG. 1 and is capable of selective cytotoxicity against tumor cells. Such selective cytotoxicity according to the definition herein, is demonstrated by activity in the in vitro cytotoxicity assay based on the continuous murine connective tissue cell line L-929 as described in PCT Publication WO 86/02381, published Apr. 24, 1986 assigned to the same assignee of the present invention and incorporated herein by reference.

The amino acid sequence of TNF is shown in FIG. 1. The sequence of FIG. 1 represents the mature or native form of human TNF. A "substantially equivalent" amino acid sequence of TNF means the amino acid sequences are identical or differ by one or more amino acid alterations (deletions, additions, substitutions) that do not cause an adverse functional dissimilarity between the altered or mutein form of the protein and native form. "Adverse functional dissimilarity" is manifest by an altered form of TNF if, in purified form, its activity in the L-929 in vitro cytotoxicity assay is destroyed. Further, individual amino acid residues in the protein may be modified by oxidation, reduction, or other derivatization, or the protein may be cleaved to obtain fragments that retain activity. Such alterations that do not destroy activity in the L-929 in vitro cytotoxicity assay mentioned above do not remove the protein sequence from the definition of TNF.

Within the foregoing definition of TNF are analogs of TNF specifically or randomly altered wherein the altered forms exhibit the selective cytotoxicity mentioned hereinabove. Such active TNF analogs or muteins ray exhibit improved properties such as increased potency in cytotoxicity assays, greater homogeneity when produced by a recombinant host, or improved processing characteristics in purification. Such TNF analogs ray also have additional functionalities not obtained in the native form, e.g., conversion of a cysteine residue leaving a free sulfhydryl in the unaltered cysteine residue that may be used to couple TNF to other moieties by formation of a disulfide or thioether bond.

Forms of TNF that are inactive in the in vitro cytotoxicity assay mentioned above may also be formed by random, site-specific or deletion mutagenesis. Although such forms do not fall within the definition of TNF herein, such forms may be useful for purposes other than causing cytotoxicity to tumor cells or direct therapy of patients having tumors susceptible to cytotoxic properties of TNF. Such forms of TNF may still potentiate or synergize the activity of other active lymphokines, for example, interleukin-2 and gamma interferon. Forms of TNF inactive in the in vitro cytotoxicity assay mentioned above may nevertheless be purified by the process disclosed herein.

Specific examples of TNF analogs include N-terminally deleted species of the protein including those having deletions of the N-terminal 1, 2, 3, 4, 5, 6, 7, 8, 9, 10, 14, and 31 amino acids as shown in FIG. 1. Also included are species of TNF in which any or all of the cysteine residues of the TNF molecule have been converted to serine or other neutral amino acids, for example, glycine or alanine. U.S. patent application Ser. No. 698,939 filed Feb. 7, 1985 assigned to the assignee of the present patent, incorporated herein by reference, discloses cysteine depleted muteins of TNF.

Deletions of C-terminal residues of TNF have also been disclosed and the mode for carrying out such deletions of up to 17 C-terminal amino acids of TNF is found in U.S. patent application Ser. No. 760,661 filed July 30, 1985, now U.S. Pat. No. 4,677,063 which is assigned to the assignee of the present invention and is incorporated herein by reference.

As to notation, for convenience, the protein having the amino acid sequence numbered 1–157 in FIG. 1 will be used as a reference and designated herein mTNF (mature TNF). All other amino acid sequences having homology with mTNF and showing TNF biological activity are referred to as "muteins" of mTNF and are denoted as to their differences from mTNF using the numbering of residues shown in the figure. For example, muteins which have substitutions for cysteine at position 69 will be denoted using the substituted residue and the position number, e.g., peptides having a serine in place of the cysteine at position 69 are designated $ser_{69}$TNF. If a residue is simply missing, it is renamed as a des-residue so that, for example, the mutein wherein the serines at positions 3 and 4 are deleted is designated $des-ser_3des-ser_4$TNF. Muteins which lack segments of amino acids at the N- or C-terminus are denoted according to the terminus affected. N-terminus deletions lacking a number of amino acids are denoted followed by $\nabla$, the number of amino acids missing. For example, muteins which lack one N-terminal amino acid as compared to the protein shown in FIG. 1 are designated $\nabla 1$TNF. For deletions at the C-terminus, the $\nabla$ will be followed by the number of the last remaining residue and a minus sign. Thus, for the mutein having 7 amino acids removed from the C-terminus, the designation would be $\nabla 150$-TNF. Where combinations of the foregoing alterations are made, the designation shows all of them, e.g., $\nabla 1des-ser_3des-ser_4ser_{69} \nabla 150$-TNF.

Not all muteins of TNF are recombinantly or deliberately produced. Indeed, the sequence obtained for the 22 N-terminal amino acids of the HL-60 secreted TNF contains minor modifications in the primary structure, although both native and recombinant proteins exhibit TNF activity. Specifically, the recombinant sequence has an additional pair of serine residues preceding the serine at position 5 before resuming the homology between positions 4–12 of the HL-60 derived protein and positions 6–14 of the deduced sequence.

As used herein, the term "TNF" is intended to include multimeric forms. TNF is known to form aggregates or multimers, predominantly dimers. Such multimers are selectively cytotoxic and are suitable for in vivo use. The TNF produced by the process according to the invention is substantially a homogeneous composition of monomeric TNF on SDS-PAGE electrophoresis.

As used herein, "chromatography" means that a subject mixture is treated with an adsorbent or other support matrix and then eluted, usually with a gradient or other sequential eluant, as opposed to a simple one step process. Material eluted from the support matrix is designated eluate. The sequential elution is most commonly done by placing the support matrix in a column and supplying an eluting solution which changes its character either stepwise or preferably by gradient. However, other methods may be used, such as placing the support matrix in a filter and sequentially administering eluants of differing character.

As used herein, "by chromatography" means that this elution must be done so as to elute less than all of the materials retained by the support matrix at one time. Thus, if done batchwise, the elution must be accomplished so as to selectively remove only the desired component while leaving the remaining materials retained by the support matrix or must comprise more than one step in which, for example, the desired component is selectively removed by first eluting the undesired component, followed by eluting the desired component retained by the support matrix.

The term "continuous hydrophobic matrix" as used herein is intended to encompass hydrophobic membranes. Such membranes are exemplified by polymers of lower alkylenes and substituted alkylenes. Polypropylene and polyethylene are examples of the former. Polytetrafluoroethylene is an example of the latter.

By "porous" is meant that the membrane has openings therein that substantially traverse the membrane. In short, a porous membrane has holes in it that go through the membrane. Such porous membranes can filter materials, allowing some portion of the material to pass through the membranes and retaining the remaining portion. "Porous" as used herein is not intended to mean pitted, i.e., having openings that do not go through the membrane.

As used herein "hydrophobic interaction matrix" means an adsorbant that is a hydrophobic solid such as polystyrene resin beads, rubber, silicon coated silica gel, or cross linked agarose sufficiently substituted with hydrophobic functional groups to render the material hydrophobic. Alkyl substituted agarose and aryl substituted agarose such as phenyl or octyl agarose are examples. Such alkyl and aryl substituents are referred to herein as hydrocarbyl. Materials to be chromatographically separated on a hydrophobic interaction chromatography (HIC) matrix are first sorbed to the HIC matrix in a high salt solution and are desorbed from the HIC matrix by elution in a low salt concentration solution or a hydrophobic solvent such as a polyol.

As used herein "anion exchange matrix" means a solid or gel support matrix that is charged in aqueous solutions. The support matrix may be agarose sufficiently substituted with amine functional groups to have a net charge in aqueous solutions. The material to be sorbed is bound to the anion exchange matrix in a low salt solution and is eluted from the anion exchange matrix in a high salt eluant containing anions such as chloride ion which bind to the anion exchange matrix and displace the sorbed material.

As used herein, "mixture" as it relates to mixtures containing TNF, refers to a collection of materials which includes TNF, but which also include other proteins. If the TNF is derived from recombinant host cells, the other proteins will ordinarily be those associated with the host. Where the host is bacterial, the contaminating proteins will, of course, be bacterial proteins. Furthermore, if the bacterial host is Gram-negative, endotoxins or lipopolysaccharide may be present. These endotoxins are routinely removed in the purification process according to the invention. However, if the TNF is associated with native sources, such proteins will be mammalian. Other non-proteinaceous materials may also be present, but generally do not constitute a purification problem.

By "high salt concentration conditions" is meant an aqueous solution wherein an ionic substance is present to create conditions of high ionic strength. Ionic strength is defined, as is understood in the art, to be calculated from the putative concentrations of the various ions placed in solution modified by their activity coefficients. Workable high salt concentrations are typified by solutions containing high concentrations of ammonium sulfate. However, other salts such as sodium chloride, potassium chloride, sodium sulfate, sodium nitrate, or sodium phosphate can be used instead, provided solubility permits and provided the same ionic strength can be obtained.

As used herein, the term "host" refers to a cell producing TNF. Such host cells may be mammalian cells that produce TNF from DNA sequences coding for TNF that are endogeneous to the genome of the cell in its native state. Preferably, the host cell will be a recombinant host cell, i.e., one into which a TNF-encoding DNA sequence has been introduced by means of recombinant molecular biological methods. Such a host cell within the definition includes eukaryotic hosts, including, for example, such mammalian cells as mentioned above into which, in addition, a TNF-encoding DNA sequence has been introduced.

Alternatively, the host cell will be a eukaryotic microorganism such as a yeast or fungus into which the DNA sequence encoding TNF has been introduced. Most preferred are prokaryotic host cells, such as members of the genuses Bacillus, Streptomyces, and Escherichia. Among Bacillus hosts, *Bacillus subtilis* is preferred. Within the genus Escherichia, *E. coli* is preferred.

The term "diafiltration" and "diafilter," as used herein, refers to a filtration process wherein the material to be filtered is maintained in a volume of liquid. Solid retained by the filter is designated retentate; liquid material passing through the filter is designated filtrate. In diafiltration processes, as the liquid filtrate is removed from the retentate across the filtering medium, liquid volume is replaced on the retentate side of the filter, preferably at a rate equal to the rate filtrate is removed. As a result, material that is capable of passing through the filter is washed from the retentate.

As used herein the term "biologically active proteins that are hydrophobic at physiological pH" refers to proteins that are hydrophobic, but soluble in a pH range between about 7.2 and 7.6. Such biologically active proteins are typified by recombinant TNF and recombinantly produced ricin toxin A chain and have the characteristic of binding to hydrophobic supports such as phenyl-TSK and phenyl agarose. The production of recombinantly produced soluble ricin toxin A chain is described in U.S. patent application Ser. No. 837,583 filed Mar. 7, 1986 and assigned to the assignee of the present patent application, and is herein incorporated by reference.

GENERAL METHOD AND PREFERRED EMBODIMENT

The process for purifying TNF according to the invention comprises two stages as shown in the flow diagram of FIG. 2. In the first stage of the process according to the invention, TNF is partially purified from a fluid containing TNF and other cell products. This TNF-containing fluid, obtained from collected disrupted TNF-producing host cells by removing the cell debris of the disrupted host cells, is filtered through a substantially continuous hydrophobic porous matrix to produce a filtrate containing a mixture enriched in TNF. To enhance the yield of the TNF in the process according to the invention, the pH conditions of the collected TNF-producing cells, their disruption and the removal of cell debris are controlled to reduce hydrolysis of the TNF. The pH conditions of the filtration of the TNF-containing fluid may be similarly controlled to maximize the TNF yield.

In a preferred embodiment of the process for purifying TNF according to the invention TNF-producing host cells are collected in a volume of fluid and the pH of the collected host cells is adjusted or maintained at a pH that reduces hydrolysis of TNF. In all of the subsequent steps of the first stage the pH of the material produced from the host cell is similarly adjusted. The collected host cells are disrupted and disrupted cell debris is removed leaving a fluid containing TNF and other cell products. This TNF-containing fluid is then passed through a continuous porous hydrophobic matrix to produce a filtrate containing a mixture enriched in TNF or a partially purified TNF.

Figure 3:
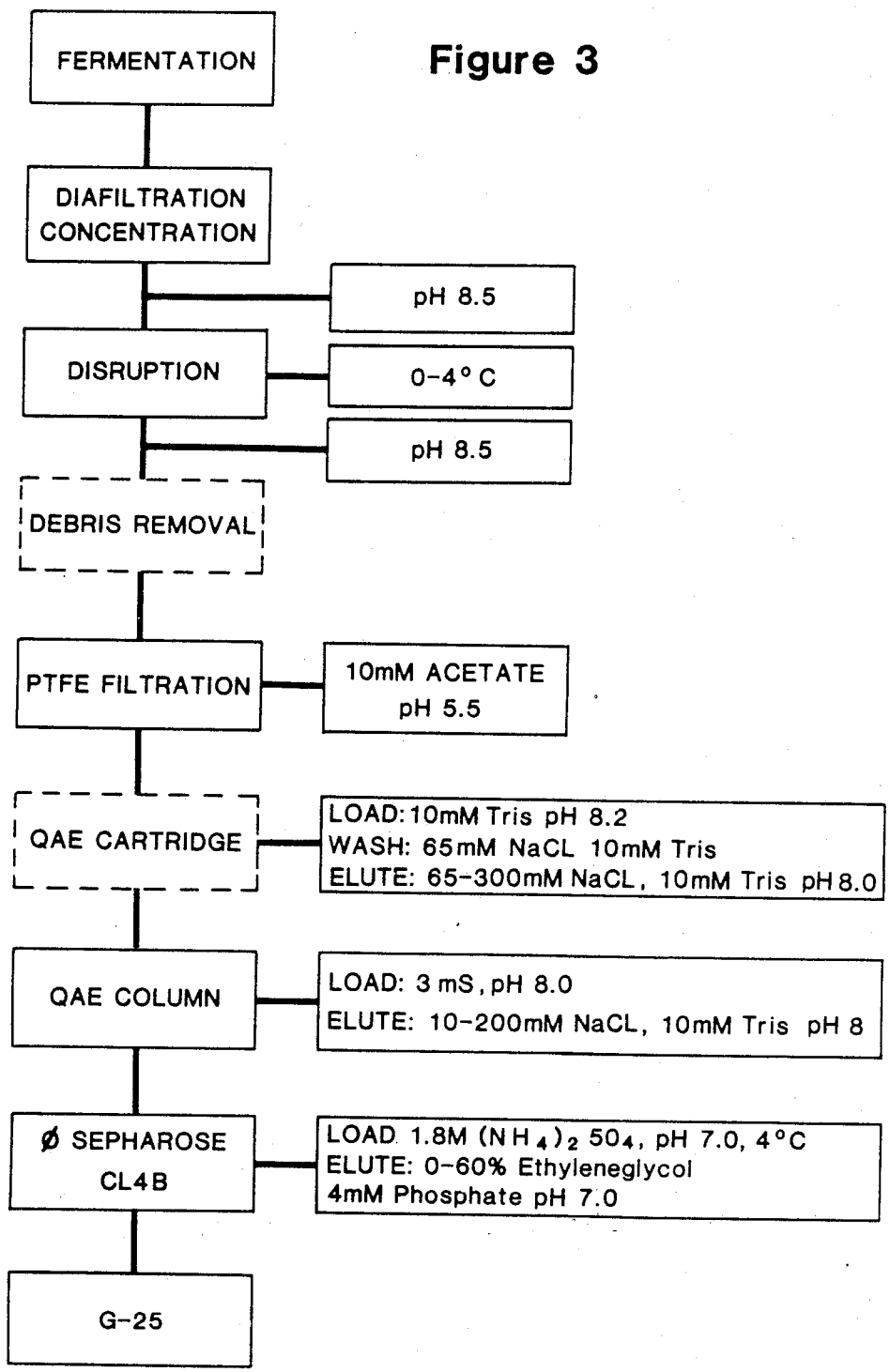
FIG. 3 is a flow diagram of an alternate preferred TNF purification process.
Figure 4:
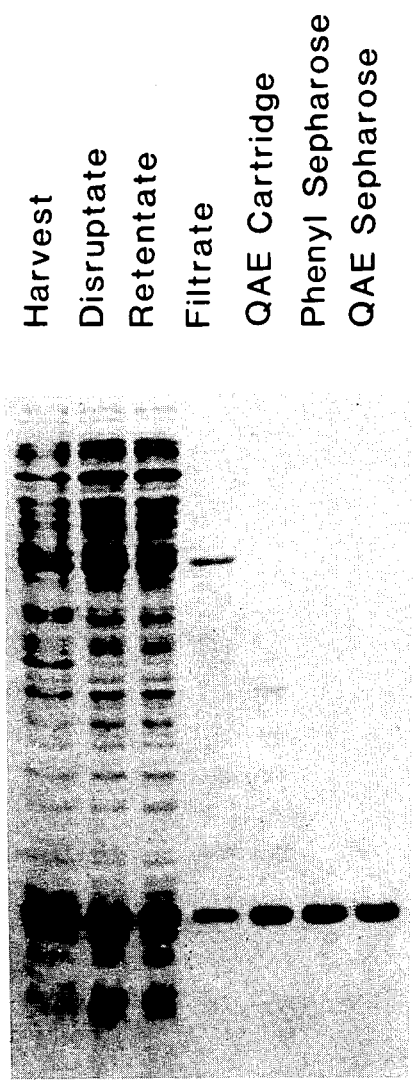
FIG. 4 is an SDS-PAGE gel of the purified product after each step of the purification process as shown in FIG. 2.
Figure 5:
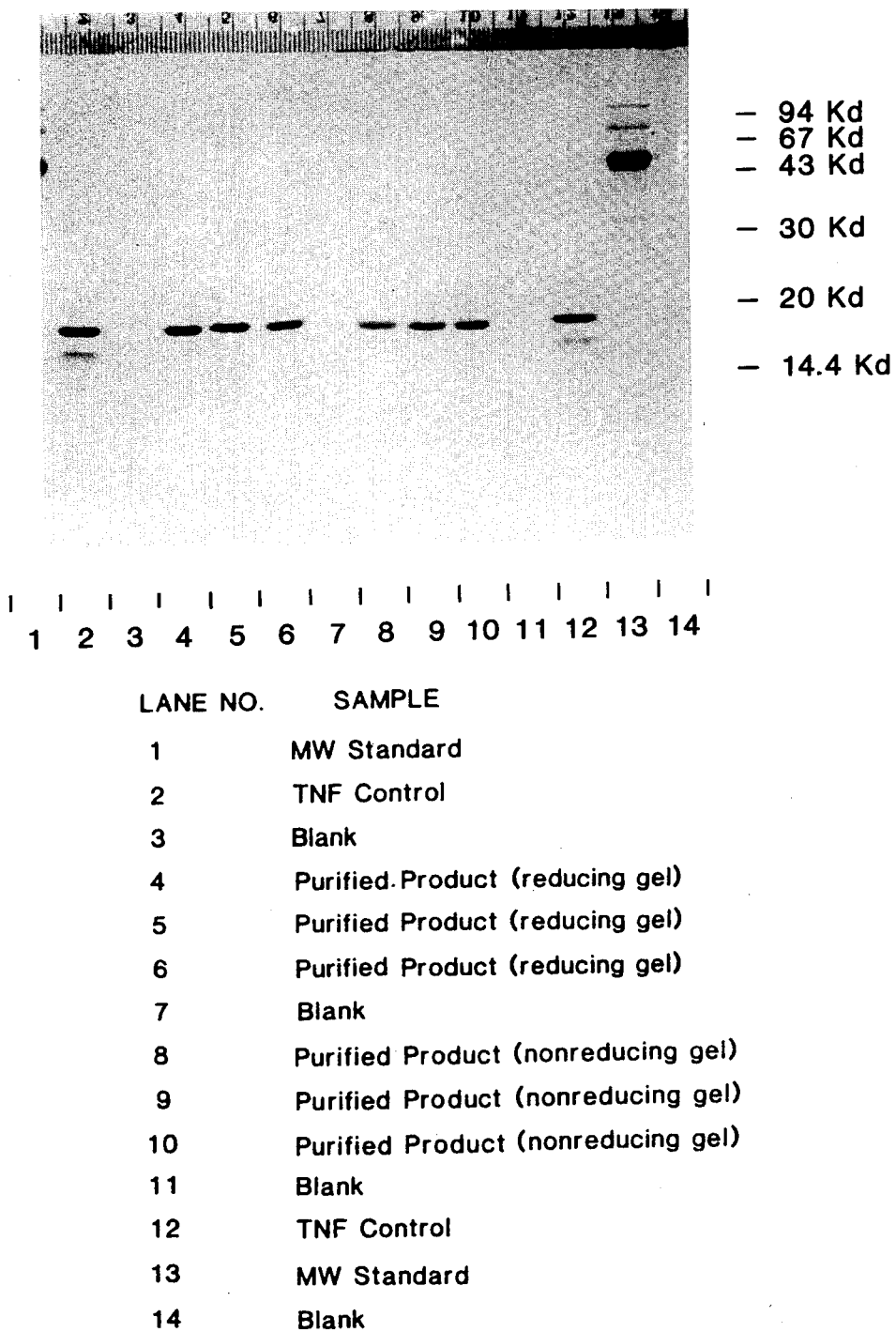
FIG. 5 is a silver stained SDS-PAGE gel of the final production run TNF.

In the second stage of the process, the mixture enriched in TNF is subjected to at least two chromatographic steps, one on a hydrophobic interaction (HIC) matrix and one on an anion exchange matrix. In one embodiment of the process, illustrated in FIG. 2, the mixture is first chromatographed on an HIC matrix and selectively eluted therefrom. The eluate so produced is substantially free of residual proteins and nucleic acid degradation products such as nucleotides and nucleosides. The material selectively eluted from the HIC matrix is then further chromatographically purified on an anion exchange matrix. Optionally, the material selectively eluted from the HIC matrix is desalted prior to this anion exchange chromatography step. A fraction high in TNF is selectively eluted from the anion exchange column using an appropriate salt. Optionally, depending upon the type and amount of salt solution used to elute the fraction high in TNF from the anion exchange matrix after the chromatography on the HIC matrix, the fraction high in TNF may require desalting on an appropriate material. In an additional option, illustrated in FIG. 3, prior to chromatographing the mixture on the HIC matrix, the mixture is chromatographed on an anion exchange matrix, and eluted therefrom with an appropriate salt solution.

The filtrate containing a mixture of TNF or partially purified TNF produced by the first stage of the process represents at least about 20% of the theoretical yield of TNF produced by the host cells. More typically the partially purified TNF amounts to between 40 and 50% of the theoretical yield of TNF produced by the cells. The mixture comprises from 40% to 70% TNF as a fraction of total protein recovered. The endotoxin level in the mixture contains between about 10 ng/ml and 10 $\mu$g/ml of the mixture.

The purified TNF recovered at the end of stage 2 of the process has a TNF content of at least 95% as determined by SDS-PAGE analysis and an endotoxin level of less than 0.1 ng/mg TNF. TNF level frequently exceeds 98% and may exceed 99%. In addition, the material is substantially free of pyrogens as determined by the USP rabbit pyrogenicity test at a dosage in a range between $1 \times 10^5$ and about $2.4 \times 10^5$ U/Kg.

In the process according to the invention, the host cell may be any one of a TNF-producing mamamalian cell, a recombinant TNF-producing eukaryotic cell. including a recombinant mammalian cell, a recombinant eukaryotic microorganism such as a yeast, for example, Saccharomyces, or other fungus such as those of the genus Aspergillus, a recombinant prokaryotic microorganism such as the Gram-positive microorganism of the genus Bacillus, including *B. subtilis* or *B. cereus*, or genus Streptomyces or Gram-negative microorganism such as the genus *Escherichia, Serratia* and the like. *E. coli* is particularly preferred.

The host cells, preferably *E. coli* transformed with a plasmid having a DNA sequence encoding TNF which is expressed by the host cell to produce TNF, are grown in a suitable growth medium to a desired cell density typically measured by optical density (OD) at 680 nm. Optical densities between about 20 and 40 are typical and an OD of about 30 is preferred.

For expression of TNF in *E. coli* transformed with a plasmid expression vector that expresses TNF under the control of most bacterial promoters, *E. coli* strain MM294, (Talmadge, K., et al., *Gene* (1980) 12:235 and Messelson, M., et al., *Nature* (1968) 217:1110), is used as the host. An appropriate MM294 strain has been deposited in the American Type Culture Collection under accession number 39,894 on Oct. 19, 1984. In such expression vectors under control of the tryptophan (trp) promoter, the trp concentration in the medium is carefully controlled to become limiting at the desired host cell density at the time TNF expression is desired.

For expression under the control of the $P_L$ promoter and gene N ribosome binding site, *E. coli* strain K12 MC1000 lambda lysogen $N_7N_5CI857SusP_{80}$, ATCC accession number 39,531 is used. Expression of TNF under control of the $P_L$ promoter is obtained by shifting the temperature from 30° to 42° C. when the desired OD of the culture is obtained.

The composition of the growth medium will, of course, depend upon the particular microorganism used. In general, an aqueous medium is used that contains assimilable sources of carbon and nitrogen, energy sources, magnesium, potassium and sodium ions, and such amino acids and purine or pyrimidine bases as required.

After the cells are harvested from the culture medium, they may be concentrated, if necessary, by filtration, centrifugation or other means. If TNF is produced as an intracellular product, it is preferred to remove from the harvested cells substantially all of the culture medium by washing the cells in an appropriate solution adjusted for pH and osmolarity so as not to prematurely break the cells or hydrolyse the desired protein product. Various means may be used to wash the cells, including low speed centrifugation so as not to shear the cells, alternating with cell washing or diafiltration. Diafiltration is preferred.

The pH of the concentrated cell suspension is also adjusted in a range that reduces hydrolysis of the TNF to be purified. pH adjustment is carried out by adding sufficient amounts of acid, preferably HCl, or base, preferably NaOH, at a concentration sufficient to reach the desired pH without degrading the protein or cells. A pH range between 5.5 and 9.5 is maintained. For TNF purification, alkaline pH is preferred and a pH of 8.5 is most preferred.

The cell membranes of the collected host cells are disrupted to release intracellular TNF. The choice of cell disruption methods will depend largely on the amount of cells harvested, but any conventional technique will be sufficient. Conventional cell disruption techniques such as homogenization, sonication, or pressure cycling ray be used. Preferred methods are sonication or homogenization with a cell homogenizer such as a Manton-Gaulin homogenizer. Cell disruption should break substantially all of the cells so that effectively no intact cells retain in the processing of the material during subsequent steps. The end point of the disruption step may be determined by monitoring the drop in the optical density of the disrupted cells to an optical density of between about 65% and 85% of the initial OD. The pH of the disrupted cell, or disruptate, will also be monitored and adjusted as necessary. pHs between 5.5 and 9.5 are acceptable. Alkaline pHs within the range are preferred and a PH of 8.5 is most preferred. pH adjustment of the disruptate may be made with suitable buffered pH solutions.

To further reduce TNF hydrolysis, it is desirable to carry out the disruption with temperature control at a temperature between 0° and 10° C. A temperature between 0° and 4° C. is preferred. Subsequent to the disruption of the host cells, the particulate matter is separated from the liquid phase of the disruptate by any conventional separation method. The removal of particulate matter at this point in the purification process is desirable because it has been discovered that cellular components associated with the cell debris can cause hydrolysis of the TNF produced by the cell.

Various means are known for removing particulate matter from the cell disruptate. Flocculating agents, such as calcium ion supplied from dissolved calcium chloride, may be added to the disruptate to aggregate suspended particulate ratter. The aggregated particulate matter in cell debris is removed by centrifugation or settling. Various appropriate flocculating agents, such as polyelectrolytes, or caking agents, such as a product sold under the tradename Filter Aid (Whatman), may be used. Various flocculating agents will be known to those skilled in the art. Centrifugation, without the use of flocculating agents, may also be used to accumulate and separate the liquid phase from the particulate matter of the disruptate.

Alternatively, the particulate matter may be separated from the liquid phase of the cell disruptate by filtering through a nonhydrophobic filter, preferably a hydrophilic cellulose ester membrane. The pore size of the filter will be selected so as to optimize the flux of the liquid phase across the filter while retaining the particulate matter. Thus, the optical pore size will depend upon the extent to which the cell material has been disrupted and whether the cell debris have been aggregated through the use of flocculating agents. Thus, appropriate pore sizes ray range from 0.01 microns to 2 microns. Pore sizes between 0.01 and 1 microns are preferred. Prior to separation of the particulate matter from the liquid phase of the disruptate, the pH of the disruptate is once again adjusted to between pH 5.5 and 9.5. Alakline pH is preferred and a pH of 8.5 is most preferred. If filtration is the method used for separating the liquid phase from the particulate ratter of the cell disruptate, cross-flow filtration is preferred.

Following separation of the liquid phase of the disruptate from the particulate matter, the liquid phase is filtered through a substantially continuous porous hydrophobic matrix. Such hydrophobic substantially continuous matrices may be made of, for example, polymers of lower alkylenes and substituted polyalkylenes such as polypropylene and polyethylene. Polytetrafluoroethylene (PTFE) is preferred. The substantially continuous porous hydrophobic matrix will generally be in the form of a membrane having a defined pore size. Such membranes may be obtained from Dorr-Oliver, Inc., Stamford, Conn. and W. L. Gore & Associates, Inc., Newark, Del. It has been found that by varying the pH, ionic strength, membrane symmetry and membrane pore size, it is possible to elute the TNF selectively and permit a small subset of proteins, including TNF, to pass through the membrane, and thereby accumulate a filtrate enriched in TNF. A pH between 5.0 and 9.5 is desirable for the filtration of TNF through the hydrophobic membrane. pHs in the acidic portion of the range are preferred and a pH of 5.5 is especially desirable. In general, any buffering system may be used so long as it can maintain the pH in the desired range. Such buffers include, for example, acetate, citrate and succinate. Ten millimolar (mM) acetate buffer has been used to good effect. Pore sizes sufficiently large to pass proteins of about 100,000 molecular weight may be used. Pore sizes from 0.1 to 3.0 microns are acceptable and a 1.0$\mu$ pore size is preferred.

Various filtration geometries may be used in filtering the liquid phase of the cell disruptate through the hydrophobic membrane. For large scale purifications, it is preferred to use diafiltration.

The material obtained after the filtration of the material through the hydrophobic membrane, at the end of the first stage of the purification process, is characterized by having a large content of TNF. Based on biological activity, approximately 50% of the TNF produced by the host cell can be recovered in the filtrate from the hydrophobic membrane. Of the protein in the filtrate, 40 to 60% of the total protein has been identified as TNF. This represents a four to six-fold purification of the TNF through the first stage of the purification process. In addition, endotoxin levels, as determined by limulus amebocyte lysate tests, range from 10 nanograms to 10 micrograms per ml of filtrate.

The steps of the recovery process subsequent to the first stage of the purification process are designed to separate the TNF from *E. coli* protein to a high level of purity, preferably at least about 95%, and more preferably at least about 98%. Simultaneously, these purification processes also reduce the levels of pyrogenic substances exogenous to TNF to a level acceptable for parenteral administration to patients. Such pyrogenicity as is detectable is believed to be inherent in the TNF molecule.

The subsequent steps in the purification of TNF are chromatographic purification steps as defined hereinabove. In an optional step the filtrate of TNF and proteins obtained at the end of the first stage is concentrated. The filtrate of TNF and protein may be concentrated by chromatography on an anion exchange matrix. The mixture is adjusted to a pH appropriate for use on the anion exchange matrix in an acceptable buffer. In general, mild alkaline pH in a range between 7.5 and 8.5 is preferable, and a pH of 8.2 is most desired. Appropriate buffers include tris(hydroxymethyl)aminoethane, glycylglycine, and triethanolamine. Ten mM Tris is preferred. Alternatively the filtrate of TNF and proteins obtained at the end of the first stage may be concentrated by ultrafiltration using a filter of a pore size sufficiently small to prevent TNF from passing through the filter. A pore size sufficient to retain proteins of molecular weight above 10,000 daltons is adequate for this purpose. In addition, the filter must be made of a material to which the TNF does not significantly adsorb so that the TNF remains substantially in the retentate. A mildly hydrophobic membrane is generally acceptable. Polysulfone membranes are preferred.

In addition to concentrating the filtrate of TNF and protein, the anion exchange matrix may be selected from those that are able to selectively remove nucleic acid degradation products such as nucleotides and nucleosides by permitting the TNF from the mixture to be selectively eluted from the anion exchange matrix in a filtrate that is substantially free of nucleic acid. Among the appropriate anion exchange resins are those that contain bound tertiary and quaternary ammonium ion. Such anion exchange matrix material is typified by QAE-agarose, QAE-cellulose, and DEAE-agarose. The mixture is loaded on an anion exchange matrix. Prior to eluting the TNF from the anion exchange matrix, the matrix is washed with a buffered salt solution, for example, NaCl. The NaCl wash selectively elutes the nucleic acid degradation products from the anion exchange matrix while selectively retaining TNF on the column at the molar concentration of the salt wash. Molar anion strengths of the wash will generally be less than 65 mM.

After the column is washed, the TNF is eluted form the anion exchange matrix in an appropriate increasing gradient of anion that is applied to the column. The eluate is monitored by optical means for absorbance in the range of 280 nm to detect the fractions of eluate containing protein as they elute from the column. The protein is eluted from the column in a salt gradient that ranges between 65 at 300 mM. Linear and stepwise gradients may be used to advantage in the process. Chloride is the preferred anion, although phosphate ion and sulfate ion are acceptable.

Provided that sufficient amounts of nucleic acid degradation products and protein have been removed in the first stage of filtering the TNF-containing fluid through the hydrophobic porous matrix, it may be desirable to completely dispense with the initial optional second stage purification step using the anion exchange column. In either event, the filtrate from the hydrophobic membrane, or the eluate from the anion exchange column, is next chromatographed on a hydrophobic interaction matrix. A number of hydrophobic interaction matrices are known and include, for example, phenyl-TSK, a resin commonly used as an HPLC support column. In general, appropriate hydrophobic supports are comprised of alkyl, phenyl, or other essentially hydrocarbyl substituents of sufficient hydrocarbon content to be hydrophobic, bound to a polymer matrix, usually a carbohydrate. Other hydrophobic polymers include polyolefins. More Preferred are alkyl agaroses as the hydrophobic interaction matrix. Phenyl agarose is particularly preferred, although octyl agarose may also be employed. The most advantageous form of alkyl agarose is one in which agarose content is between about 3.5 and about 8%, and is crosslinked. More preferred are phenyl aragose resins in which the agarose content is between 4 and 6% and crosslinked. Most preferred is a phenyl agarose having 6% crosslinked agarose. A product of Pharmacia Corporation (Uppsala, Sweden), called Fast Flow Phenyl Sepharose, is particularly preferred.

In addition, macroporous substrates that are alkyl or phenyl substituted are in general of sufficient hydrophobicity to serve as a hydrophobic interaction matrix. In addition, various silicas also meet this criterion. In general, any hydrophobic material that will bind TNF under high salt conditions within the pH range of from 4 to 9 may be used, although those that bind in a pH range between 5 and 9 are preferred.

Prior to loading the column with the mixture or filtrate, the column is equilibrated with a high salt solution. Workable high salt concentrations are typified by solutions containing high concentrations of ammonium sulfate. Other salts such as sodium chloride, potassium chloride, sodium phosphate, sodium sulfate, magnesium sulfate, and sodium nitrate, can be used provided that solubility permits, and provided that the same ionic strength can be obtained. In a preferred mode, the column is equilibrated with ammonium sulfate, in a range between 1.5 and 2 molar. Preferably, the sodium sulfate is used at a concentration of 1.8 molar. Four molar sodium chloride can also be used.

The eluate or filtrate is brought to high salt concentration as defined above and is loaded on the column. In general, the high salt concentration is achieved by adding ammonium sulfate to between 1.5 and 2 molar, preferably 1.8 molar. The pH of the high salt solution is maintained between about 5 and 7. A PH of 5.5 is preferred. The column and the material bound thereto al this high salt concentration is maintained at a temperature in a range between 0° and 25° C. It is generally preferred that the material and column be maintained at a temperature well below 25° C. during this step, with 4° C. being preferred.

The TNF protein is eluted from the hydrophobic interaction matrix at a low salt concentration. The particular salt concentration will depend upon the mutein form of the TNF molecule chromatographed and on the particular hydrophobic interaction matrix used. In general, the TNF material elutes as the salt concentration drops. The particular salt concentration at which the TNF elutes will also depend somewhat upon the buffer used.

Various materials may be used to elute the TNF from the column, including various chaotropic agents and nonionic detergents. Polyols ray also be used so long as they remain substantially flowable at the temperature at which the column is maintained. Propylene glycol and ethylene glycol may be used. A linear gradient of ethylene glycol in an appropriate buffer in a range of from 0 to 60% ethylene glycol is preferred. As indicated above, the buffer may vary and the pH may range between 5 and 8. Four mM acetate buffer may be used at a pH of about 5. A pH of 5.5 is preferred.

Optionally, the material eluted from the hydrophobic interaction matrix may be desalted. Preferably, the material is desalted using a size exclusion resin such as G-10, G-15 or G-25 Sephadex.

Once eluted from the hydrophobic interaction matrix, the protein solution or optionally desalted protein solution is chromatographed on an anion exchange matrix. Any anion exchange matrix can be used which will selectively bind the protein and allow the chaotropic agent or detergent to pass so that the bound protein may be eluted. Such anionic exchange matrices are well known to those skilled in the art and in ge co substituted amines in an agarose or cellulose matrix. Trisubstituted and quaternary substituted amines are particularly preferred. Diethylaminoethyl (DEAE) agarose is one such ionic exchange matrix. Quaternary substituted agarose and cellulose are also suitable. A convenient commercial quaternary ammonium anionic exchange medium is sold under the tradename Fast Flow Q Sepharose (Pharmacia, which is a bound quaternary ammonium ion containing matrix.

As mentioned above, prior to loading the protein solution eluted from the hydrophobic interaction matrix onto the anion exchange matrix, the protein solution ray be optionally desalted. If the Protein solution eluted from the hydrophobic interaction matrix is not desalted, then the eluate is diluted with double distilled deionized water to decrease the ionic strength of the solution so that the protein will bind to the column. Ionic strength of the material is determined by monitoring the conductivity of the solution so that it is below 3 millisiemens (mS). In general, a conductivity of approximately 2 mS is preferred. The pH of the solution is adjusted to between about 7 and 9. A pH of 8 is preferred. Prior to loading the pH-adjusted eluate on the column, the column is equilibrated with buffer. Sodium phosphate, Tris sulfate or Tris chloride are appropriate. Ten mM is preferred.

A salt gradient is used to elute the TNF protein selectively from the column. A sodium chloride or sodium sulfate gradient may be used. The salt gradient is buffered with an appropriate buffer which is generally the same as the one used to equilibrate the column. The pH of the buffer is again maintained between 7 and 9, preferably at pH 8. If sodium sulfate will be used as the eluting salt gradient, for example, Tris sulfate will be used as the buffer. The salt gradient ranges between 0 mM to 200 mM.

The protein is collected in fraction of equal aliquots as it comes off the column and is monitored for protein concentration at 280 nanometers in a spectrophotometer. Optionally, in the event that Tris buffer is used, a desalting step using a sizing column is required if the material is to be used for therapeutic purposes. G-10, 15 or 25 Sephadex are appropriate size exclusion resins.

The invention will be more clearly understood in relation to the following examples which are intended by the applicant to be merely exemplary and non-limiting.

EXAMPLE I

Growth of Recombinant TNF-Producing Host Cells

A. A fermenter was filled with distilled deionized water to operating volume and the following materials were added to the indicated final concentrations: $ZnSO_4.7H_2O$, 60 $\mu M$; $MnSO_4.H_2O$, 60 $\mu M$; $CuSO_4.5H_2O$, 2 $\mu M$; $Na_3citrate.2H_2O$, 1.5 mM; $KH_2PO_4$, 21.6 mM; $(NH_4)_2SO_4$, 72 mM. The medium was sterilized in the fermenter. The pH of the medium was adjusted to 6.5±0.1 with KOH. 50% glucose, KOH and antifoam were added by sterile feeds to the fermenter to achieve a 5 g/l glucose concentration. The following solutions were also added to the indicated final concentrations: 100 $\mu M$ $FeSO_4.7H_2O$, 20 mg/l thiamine HCl; 3 mM $MgSO_4.7H_2O$.

B. *Inoculum:* A stock culture of *E. coli* K12 strain DG95λ transformed with plasmid pAW740A, the tranformant having ATCC Accession No. 53332, was thawed and grown at 30° C. to an optical density of 50-100 Klett units in flasks using double strength Luria broth with 10% NaCl, 5 mg/100 ml ampicillin and frozen in vials. One raster stock vial was grown in Luria broth as above, but without ampicillin. Culture was diluted to 10% in glycerol and dispensed into vials and frozen at −70° C. to be used as working stock.

A container of the working stock was thawed, grown in 2× Luria broth at 30° C. to approximately 1 $OD_{680}$, then added to the fermenter to a final cell concentration of 1 mg/liter.

C. *Growth Conditions*: Temperature was maintained at 30° C.±1° C., dissolved $O_2$ concentration was 40% air saturation and pH was controlled at 6.8 by automatic addition of 5 N KOH. Optical density was monitored. When the culture reached an $OD_{680}$ of 15 units, the temperature was raised to 42° C. to induce TNF production and casamino acids were added to 2%. Cells were harvested about four hours after casamino acid addition.

EXAMPLE II

Concentration and Diafiltration

The harvested material was concentrated approximately 5-fold by circulating it under pressure past a hollow fiber microporous (0.2 $\mu$) polypropylene membrane. Residual medium was removed by diafiltration against 5 volumes of deionized water. The retentate was kept and the pH adjusted to 8.2.

EXAMPLE III

Cell Disruption

The concentrated cell suspension was disrupted by multiple passages through a Manton-Gaulin high pressure homogenizer at 6000 to 8000 psig. After disruption the system was washed with deionized water. The disruptate and rinse water were retained and the pH adjusted to 8.2.

EXAMPLE IV

Diafiltration on Hydrophobic Membrane at pH 5.5

The cell disruptate and rinse water were pH adjusted to 5.5 with glacial acetic acid. The pH adjusted material was diafiltered against 5 volumes of 10 mM acetate buffer using a Dorr-Oliver diafiltration device and a polytetrafluoroethylene membrane having a 1.0$\mu$ pore size; Door-Oliver part number GFI16-D10868-1. The filtrate was collected.

EXAMPLE V

Diafiltration on Hydrophobic Membrane at pH 8.5

The cell disruptate and rinse water were treated as in Example IV except that a pH of 8.5 was maintained using 10 mM Tris buffer

EXAMPLE VI

Removal of Disrupted Cell Debris:Centrifugation

The cell disruptate and rinse water of Example IV were pH adjusted using Tris and NaOH to 8.2 as necessary and the flocculating agent $CaCl_2$ was added to aggregate cell debris. The aggregate was separated from the supernatant by centrifugation at 14000 xg in a Sorvall RC-3B centrifuge. The supernatant was retained and treated as in Example IV and V.

EXAMPLE VII

Removal of Disrupted Cell Debris:Diafiltration

The cell disruptate and rinse water of Example IV were pH adjusted using Tris and NaOH to 8.2. The material was diafiltered under pressure at 15 psi against 5 volumes of distilled water using a crossflow hydrophilic cellulose ester hollow fiber cartridge (Model KF-200-10, Microgon, Laguna Hills, CA). The filtrate was retained and the pH was adjusted and treated as in Example IV or V.

EXAMPLE VIII

Concentrating the Filtrate

A. Anion Exchange Chromatography

Tris was added to the filtrate of Example IV to a concentration of 10 mM and the pH adjusted if necessary to 8.2 with glacial acetic acid or NaOH. An anion exchange column containing quaternary ammonium ion (Zeta prep-250 QAE cartridge) was equilibrated with 10 mM Tris and the filtrate was loaded onto the cartridge. The loaded material was washed with 65 mM NaCl, 10 mM Tris, pH 8.0. A low molecular weight fraction absorbing at 260 nM eluted with the 65 mM salt wash. A linear 65–300 mM NaCl gradient in 10 mM Tris, pH 8.0 maintained by an Eldex gradient controller is used to elute the TNF while monitoring the eluate for protein by absorbance at 280 nM. The protein fraction elutes from the column to yield a TNF-containing eluate having a volume approximately one-twentieth of the filtrate loading volume, and substantially free of nucleic acid degradation products absorbing at 260 nM.

B. Ultra Filtration

The TNF-containing filtrate of Example IV was concentrated 10 to 20-fold by ultrafiltration on a 10,000 molecular weight cut off polysulfone membrane (Dorr-Oliver part #16-D10864-01). The TNF remained in the retentate and the retentate was subsequently treated as in Example IX.

EXAMPLE IX

Phenyl Sepharose Chromatography of Filtrate $(NH_4)_2SO_4$ was added to the filtrate containing TNF obtained in Example IV to a concentration of 1.8 M and the pH was measured and adjusted to 7.0. The material was filtered through a 0.45 micron filter. The filtrate was loaded onto a phenyl Sepharose CL4B column (Pharmacia, Uppsala, Sweden) after first equilibrating the column with 1.8 M $(NH_4)_2SO_4$ in sodium phosphate buffer at pH 7.0. Using an Eldex gradient controller (Eldex Laboratories, Inc., San Carlos, CA), a linear gradient of 100% 1.8 M $(NH_4)_2SO_4$, in 10 mM sodium phosphate buffer, at pH 7.0 to 100% of 60% ethylene glycol in 4 M sodium phosphate buffer pH 7.0, was used to elute the protein from the column. The eluate fractions were monitored for protein concentration at 280 nM and those fractions of TNF falling within 80% of the maximum peak height on the ascending and descending legs of the plot of protein concentration of the eluate fractions were retained and pooled.

EXAMPLE X $(NH_4)_2SO_4$ was added to the TNF-containing eluate of Example VIII.A or the retentate of Example VIII.B to a concentration of 1.8 mM, adjusted to pH 7.0 with HCl and filtered through a 0.45 $\mu$M filter. The sample was subsequently chromatographed on phenyl Sepharose CL4B as in Example IX.

EXAMPLE X

The pooled eluate from the phenyl Sepharose column is desalted by chromatography on a G-25 Sephadex column equilibrated with 10 mM Tris buffer pH 9.2. The fast eluting fraction detected by absorbance at 280 nM is collected and subsequently treated as in Example XI, XII or XIII except that the dilution with deionized water is omitted unless necessary to achieve a conductivity of less than 2.2 ms.

EXAMPLE XI

The pooled eluate fractions obtained from the phenyl Sepharose column were diluted with deionized water to a conductivity less than 2.2 mS and the pH was adjusted to 8.2 with NaOH. A QAE Sepharose column (Pharmacia) was equilibrated with 10 mM sodium phosphate buffer at pH 8.2 prior to loading the diluted pooled fractions on the column. A linear gradient of 10 mM to 200 mM sodium phosphate buffer PH 8.2 was used to elute the TNF protein from the column. The eluate is monitored at 280 nM for protein concentration of the eluate fractions. The TNF peak falling within 90% of the maximum height on the ascending and descending legs of a plot of eluate fraction protein concentration is retained.

EXAMPLE XII

The pooled eluate fractions from the phenyl Sepharose column were diluted as in Example XI except that 10 mM Tris at pH 8.0 was used. The QAE Sepharose column was equilibrated with 10 mM Tris.HCl buffer at pH 8.0 prior to loading the diluted pooled fractions on the column. A linear 10 to 200 mM NaCl gradient in 10 mM Tris pH 8.0 was used to elute the TNF from the column. The eluate was monitored and fractions pooled as in Example XI.

EXAMPLE XIII

The pooled fractions from the phenyl Sepharose column were handled as in Example XII except that 10 mM Tris.SO$_4$ pH 8.0 was used to dilute the sample and equilibrate the column. A 10 to 200 mM linear sodium sulfate gradient in 10 mM Tris.sulfate pH 8.0 was used to elute the TNF. Protein concentration was monitored and the TNF fractions were pooled as in Example XI.

EXAMPLE XIV

Pooled eluates of Examples XII and XIII are desalted using a G25 Sephadex column equilibrated with 10 mM NaPO$_4$ at pH 8.0. The fast eluting fraction was monitored for protein concentration at 280 nM, pooled and retained.

EXAMPLE XV

Determination of TNF Potency-Assay of Biological Activity

TNF activity is quantitatively measured using an in vitro cell cytotoxicity assay utilizing a TNF sensitive murine L-929 fibroblast target cell line. Murine L-929 fibroblast cells (ATCC CCL 1.2) are grown in Eagle's Minimum Essential Medium (MEM) with Earle's salts, 10% fetal bovine serum (FBS) and 1% penicillin-streptomycinfungizone solution, at 37° C. (5% CO$_2$). A master stock of the cell culture is stored in liquid nitrogen. Working stocks are subcultured twice weekly and maintained for 30 passages. 96-well flat-bottomed trays containing confluent monolayers of the L-929 cells are prepared by adding 75 μl of 2.6×10$^5$ trypsinized cells/ml to each well and then incubating the plates for 18 hours at 37° C. (5% CO$_2$). Cell monolayers are prepared one day prior to sample addition.

Samples are serially diluted in a separate dilution plate and transferred to the cell plates to which actinomycin-D has been added to a final concentration of 1 μg/ml immediately prior to sample transfer. Cytotoxicity is scored the following day by spectrophotometrically measuring neutral red dye uptake by viable cells. One unit of TNF activity is defined as that amount required for 50% cell killing. This actinomycin-D enhanced cytotoxicity assay is adapted from those described by J. M. Ostrove and G. E. Gifford in *Proc. Soc. Exp. Biol. Med.*, 160:354–358 (1979) and M. R. Ruff and G. E. Gifford in *Inf. Imm.*, 31:380–385 (1981). Scoring cytotoxicity using neutral red staining is modified from the procedure described by F. C. Kull and P. Cuatrecasas in *J. Immunol.*, 126:1279–1283 (1981).

TNF activity of the sample is determined in comparison to a TNF standard prepared from the final purification product of Examples XI, XII, XIII or XIX. To prepare the TNF standard, TNF final purification product is diluted with MEM Earl's salts medium containing 2% FBS and 1% penicillin-streptomycin-fungizone solution. The diluted material is aliquoted and stored at −70° C. The L-929 cytotoxicity assay, run on at least six different days, is used to titer the standard, setting 1 unit TNF/ml as the amount of TNF producing 50% cell killing.

As a control, a preparation of TNF is aliquoted into vials, and stored at −70° C. In each assay, a vial is assayed along with the other samples for the purpose of evaluating inter-assay variability.

The quantitative measurement of the TNF activity of a sample is performed as follows:

The sample is diluted in assay medium (MEM Earl's salts medium containing 2% FBS and 1% penicillin-streptomycin-fungizone solution) to estimated TNF concentrations between 10$^4$ and 10$^5$ units/ml.

An aliquot of the TNF control sample is diluted in assay medium to estimated TNF concentrations between 10$^4$ and 10$^5$ units/ml.

96-well trays are filled with 120 μl/well assay medium. 60 μl of one of the following TNF solutions is added to the first well of each row and is serially diluted 1:3 down each row:

a. The sample to be assayed.
b. TNF control sample.
c. In-house TNF standard.

The sample plates are UV sterilized for 10 minutes and then incubated for approximately 10 minutes at 37° C. (5% CO$_2$).

25 μl/well of actinomycin-D (1 μg/ml final concentration) is added to 96-well flat-bottomed trays containing confluent monolayers of L-929 cells (75 μl), and within two hours 100 μl/well of the serially diluted samples is added. Assay plates are incubated for 18 hours at 37° C. (5% CO$_2$) and the cells are stained with 50 μl/well of neutral red (0.075%)/glutaraldehyde (10.17%) solution. Plates are incubated for one hour at 37° C. (5% CO$_2$) and excess staining solution is removed. Plates are washed with 600 μl/well of PBS. 100 μl/well of stain solubilizing solution (3% SDS, 0.04 N HCl in 2-propanol) is added and the plates are shaken for one minute. Absorbance is read at 550 nm using a plate reader.

From the dilution factor required to each 50% cell killing, plate-to-plate variation is corrected by means of the in-house TNF standard. The cytotoxicity activity in the pre-diluted samples is calculated and expressed as units/ml. If the sample was diluted the activity is multiplied by the pre-dilution factor to obtain the units/ml in the sample.

TNF concentration and specific activity can be determined with this information and the protein concentration obtained by standard Lowry test.

EXAMPLE XVI

Protein Purity Assay:SDS-PAGE

To determine the purity of the TNF protein, the final purification product is analyzed by SDS-polyacrylamide gel electrophoresis (SDS-PAGE), which separates proteins by molecular sizing. Quantitative measurement of protein impurities is obtained from Fast Green-stained gels. The qualitative but highly sensitive evaluation of impurities is obtained from silver-stained gels. The quantitative measurement of protein impurities in the final purification product is performed on both reducing and non-reducing gels using Fast Green-staining as follows:

For reducing gels, TNF final purification product is diluted in buffered 2-mercaptoethanol solution (10% mercaptoethanol, 18% glycerol, 4% SDS and 0.11 M Tris pH 6.8) to a concentration of about 0.25 mg/ml. This protein solution is heated for three minutes at approximately 95° C. Calibration proteins are treated in an identical manner.

For non-reducing gels, TNF final purification product is diluted in buffered solution (20% glycerol, 4% SDS and 0.12 M Tris pH 6.8) to a concentration of about 0.25 mg/ml and this protein solution is heated for three minutes at approximately 95° C.

The SDS-PAGE apparatus (Hoeffer Scientific Instruments, Model SE-40) is set up containing a 1.5 mm thick gel of a linear 10–15% acrylamide gradient. Approximately 7 μg protein/gel lane (at least 2 lanes per sample), is loaded and electrophoresed. After electrophoresis, the gel slab is stirred in a solution containing 1% Fast Green and 7% acetic acid. The gel is destained with a solution containing 5% methanol and 7% acetic acid and scanned on a densitometer at wavelength 635 nm.

The area of the main peak (assignable to TNF) is measured, divided by the total area measured in the scan (areas due to inclusions in the gel or scratches on the gel carrier plate are subtracted from the total area measurement) and multiplied by 100, to determine the percent of the staining area that is attributable to TNF.

The qualitative evaluation of impurities in the final purification product is performed on both reducing and non-reducing gels using silver-staining. Gels 0.75 mm thick of 15% acrylamide are used. Approximately 1 μg of protein is loaded into a lane. After electrophoresis, silver-staining is accomplished by placing the gel slab in a fixing solution of ethanol/acetic acid, then in a staining solution of silver nitrate/sodium hydroxide-ammonium hydroxide, and finally in a developing solution of formaldehyde/citric acid. The gels are then photographed. A representative silver stained gel is shown as FIG. 2.

EXAMPLE XVII

Protein Purity Assay - Isoelectric Focusing

To determine the purity of the TNF protein, the product also is analyzed by isoelectric focusing (IEF), which separates proteins by their isoelectric point (pI). The qualitative but sensitive evaluation of protein species is obtained from Coorassie Blue-stained gels. The measurement of protein species in the product is performed on polyacrylamide gels as follows:

The IEF flat bed apparatus FBE 3000 (Pharmacia) is set up with a pH 4.0–6.5 Ampholine polyacrylmide gel (PAG) plate and a pH 3.5–9.5 Ampholine PAG plate. Approximately 3 μg protein is loaded per gel lane for each sample and 10 μg/gel lane for the pI standards.

The sample is electrofocused and after electrofocusing, the gels are placed in a fixing solution containing 3.8% 5-sulfosalicylic acid, 12% trichloroacetic acid and 30% methanol. The gels are washed with a solution containing 25% ethanol and 8% acetic acid and stained in a solution containing 0.09% Coomassie Brilliant Blue R, 25% ethanol and 8% acetic acid.

The gels are destained with a solution containing 25% ethanol and 8% acetic acid.

EXAMPLE XVIII

The Limulus Amebocyte Lysate (LAL) test, as described in USP XX, page 888, is used to assess the level of endotoxin present in the final purification product. Lyophilized preparations of lysate and control standard endotoxin are obtained from licensed vendors for use in the test. The LAL test on the final purification product is performed as follows:

Final purification product is suspended in Sterile Water for Injection, U.S.P. Four replicate 2-fold dilution series for the suspended product and for the control standard endotoxin using Sterile Water for Injection, U.S.P. as diluent are prepared. Negative controls consisting of the sterile water diluent only and positive controls consisting of the same diluent inoculated with endotoxin at a level of not more than two times the stated lysate sensitivity are included.

Lysate is added to each tube and the tube is incubated at 37°±1° C. for 60±2 minutes and read. The concentration of endotoxin in the sample is calculated by the formula (pλ) (f/Σ) as described in USP XX.

For an acceptable test, the following conditions must be met:

The lysate sensitivity obtained in the test must be within one serial dilution of the labeled sensitivity. The negative control must exhibit no gelation and firm gelation must occur in the positive control(s).

EXAMPLE XIX

The product of Example XIV is diluted in 20 mM sodium phosphate pH 7.5 concentration sufficient to yield a predetermined specific activity when mixed with a solution of 20% mannitol. 20% mannitol is added and the formulated product is prefiltered through a 0.45 μM filter. The formulated product is lyophilized.

EXAMPLE XX

The desalted product of Example XV is obtained and formulated as in Example XIX.

It will be readily appreciated by those skilled in the art that the processes and compositions according to the invention may be varied without departing from the essence of the invention as disclosed and claimed. Such variations to the process or the compositions obtained thereby are intended to be within the scope of the invention.

It further will be readily appreciated by those skilled in the art that the above-described purified TNF may be formulated with any one of a number of well known pharmaceutically acceptable carriers, depending upon the optical route of administration, e.g., parenteral, including intravenous, intraperitoneal, intramuscular and subcutaneous. Such carriers include solutions compatible with the mode of administration and solubility of the compounds. Such solutions may be buffered or otherwise formulated to minimize undesirable localized effects of injection if necessary.

For parenteral use, the compounds of this invention can be formulated with sterile ingredients compounded and packaged aseptically. They may be administered intravenously or intramuscularly. Useful solvents for formulation in such use are the polyhydric aliphatic alcohols and mixtures thereof. Pharmaceutically acceptable glycols, such as propylene glycols, and mixtures thereof, or glycerine may be employed. Pharmaceutically acceptable sugar alcohols such as mannitol or sorbitol may be used. Water may be incorporated in the vehicle if desired.

A pH range of about 7.4 and isotonicity compatible with body isotonicity, are desirable. Basicity may be controlled by the addition of a base as required. It may often be desirable to incorporate a local anesthetic, and such are well known to those skilled in the art. The percentage of the compound to be used in the pharmaceutical carrier may be varied. It is necessary that the compound constitute a proportion such that a suitable dosage will be obtained.

The dosage required to achieve the desired pharmacologic activity in the mammal will vary with various factors such as route of administration, the species of mammal, general health and tolerances of the mammal, weight, sex and age of the mammal, the nature and severity of the disease being treated and the like. Additionally, it is to be noted that the exact dosage of each individual compound employed in similar situations will vary.

What is claimed is:

1. A purified TNF composition wherein the TNF is N-terminally deleted, lacking from 1 to 10 amino acids, and is substantially free of pyrogens as determined by the USP rabbit pyrogen test at a dosage range of about 1.0 to $2.4 \times 10^5$ U/Kg, and is substantially non-bindable to a hydrophobic porous membrane.

2. The purified TNF composition of claim 1 wherein the N-terminally deleted TNF is selected from the group consisting of minus 1 through minus 10 TNF.

3. The purified TNF composition of claim 2 wherein the TNF is minus 8.

4. The purified TNF composition of claim 2 wherein the TNF is minus 7.

5. The purified TNF composition of claim 2 wherein the TNF is minus 6.

6. The purified TNF composition of claim 2 wherein the TNF is minus 4.

7. The purified TNF composition of claim 2 wherein the TNF is minus 2.

8. The purified TNF composition of claim 1 wherein said hydrophobic porous membrane is constructed of materials selected from the group consisting of polytetrafluroethylene, polypropylene and polyethylene.

9. The purified TNF composition of claim 1 wherein said porous hydrophobic membrane consist of polytetrafluroethylene.

* * * * *